US010293039B2

(12) United States Patent
Freitag et al.

(10) Patent No.: US 10,293,039 B2
(45) Date of Patent: May 21, 2019

(54) **ATTENUATED *LISTERIA MONOCYTOGENES* MUTANT AS A VACCINE VECTOR FOR THE DELIVERY OF EXOGENEOUS ANTIGENS**

(71) Applicants: The Board of Trustees of the University of Illinois, Urbana, IL (US); Montana State University, Bozeman, MT (US)

(72) Inventors: Nancy Freitag, Mundelein, IL (US); Joshua Obar, Bozeman, MT (US)

(73) Assignees: The Board of Trustees of the University of Illinois, Urbana, IL (US); Montana State University, Bozeman, MT (US)

(*) Notice: Subject to any disclaimer, the term of this patent is extended or adjusted under 35 U.S.C. 154(b) by 0 days.

(21) Appl. No.: 14/680,397

(22) Filed: Apr. 7, 2015

(65) Prior Publication Data

US 2015/0283221 A1    Oct. 8, 2015

Related U.S. Application Data

(60) Provisional application No. 61/976,144, filed on Apr. 7, 2014.

(51) Int. Cl.
*A61K 39/00* (2006.01)
*A61K 39/02* (2006.01)

(52) U.S. Cl.
CPC .... *A61K 39/0208* (2013.01); *A61K 2039/522* (2013.01); *A61K 2039/523* (2013.01)

(58) Field of Classification Search
None
See application file for complete search history.

(56) References Cited

U.S. PATENT DOCUMENTS

| 2002/0136737 | A1  | 9/2002  | Frankel | 424/200.1 |
|---|---|---|---|---|
| 2003/0202985 | A1  | 10/2003 | Paterson | 424/200.1 |
| 2015/0283221 | A1* | 10/2015 | Freitag | A61K 39/0208 424/200.1 |

OTHER PUBLICATIONS

Kotton et al, Infection and Immunity, Oct. 2004, 72/10:5535-5547.*
Alonzo et al, Infection and Immunity, Nov. 2010, 78/11:4944-4957.*
Wilson et al, Infection and Immunity, Jan. 2006, 74/1:765-768.*
Cahoon et al, Infection and Immunity, Oct. 2015, 83/10:4028-4040.*
Wood et al, Frontiers in Cellular and Infection Microbiology, May 2014. vol. 4, Article 51, 22 pages (Year: 2014).*
Alonzo et al. "The Posttranslation Chaperone PrsA2 Contributes to Multiple Facets of *Listeria monocytogenes* Pathogenesis" Infection and Immunity 2009 77(7):2612-2623.
Alonzo, F. and Freitag, N. E. "*Listeria monocytogenes* PrsA2 Is Required for Virulence Factor Secretion and Bacterial Viability within the Host Cell Cytosol" Infection and Immunity 2010 78(11):4944-4957.
Angelakopoulos et al. "Safety and Shedding of an Attenuated Strain of *Listeria monocytogenes* with a Deletion of actA/plcB in Adult Volunteers: a Dose Escalation Study of Oral Inoculation" Infection and Immunity 2002 70(7):3592-3601.
Archambaud et al. "Control of *Listeria* Superoxide Dismutase by Phosphorylation" The Journal of Biological Chemistry 2006 281(42):31812-31822.
Beveridge, T. J. and Murray, R. G. E. "Sites of Metal Deposition in the Cell Wall of *Bacillus subtilis*" Journal of Bacteriology 1980 141(2):876-887.
Bierne et al. "Internalins: a Complex Family of Leucine-Rich Repeat-Containing Proteins in *Listeria monocytogenes*" Microbes and Infection 2007 9:1156-1166.
Boujemaa-Paterski et al. "Listeria Protein ActA Mimics WASP Family Proteins: It Activates Filament Barbed End Branching by Arp2/3 Complex" Biochemistry 2001 40:11390-11404.
Cascales, E. "The Type VI Secretion Toolkit" EMBO Reports 2008 9(8):735-741.
Chatterjee et al. "Intracellular Gene Expression Profile of *Listeria monocytogenes*" Infection and Immunity 2006 74(2):1323-1338.
Desvaux et al. "Secretion and Subcellular Localizations of Bacterial Proteins: a Semantic Awareness Issue" Trends in Microbiology 2009 17(4):139-145.
Desvaux, M. and Hébraud, M. "The Protein Secretion Systems in *Listeria*: Inside Out Bacterial Virulence" FEMS Microbiology Review 2006 30:774-805.
Domann et al. "A Novel Bacterial Virulence Gene in *Listeria monocytogenes* Required for Host Cell Microfilament Interaction with Homology to the Proline-Rich Region of Vinculin" The EMBO Journal 1992 11(5):1981-1990.
Donnenberg, M. S. "Pathogenic Strategies of Enteric Bacteria" Nature 2000 406:768-774.
Dramsi, S. and Cossart, P. "Listeriolysin 0-Mediated Calcium Influx Potentiates Entry of *Listeria monocytogenes* into the Human Hep-2 Epithelial Cell Line" Infection and Immunity 2003 71(6):3614-3618.
Gaillard et al. "Entry of L. monocytogenes into Cells Is Mediated by Internalin, a Repeat Protein Reminiscent of Surface Antigens from Gram-Positive Cocci" Cell 1991 65:1127-1141.
Gerlach, R. G. and Hensel, M. "Protein Secretion Systems and Adhesins: the Molecular Armory of Gram-Negative Pathogens" International Journal of Medical Microbiology 2007 297:401-415.
Glomski et al. "The *Listeria monocytogenes* Hemolysin Has an Acidic pH Optimum to Compartmentalize Activity and Prevent Damage to Infected Host Cells" The Journal of Cell Biology 2002 156(6):1029-1038.
Gray et al. "How the Bacterial Pathogen *Listeria monocytogenes* Mediates the Switch from Environmental Dr. Jekyll to Pathogenic Mr. Hyde" Infection and Immunity 2006 74(5):2505-2512.

(Continued)

*Primary Examiner* — Nita M. Minnifield
(74) *Attorney, Agent, or Firm* — Licata & Tyrrell P.C.

(57) ABSTRACT

Vaccines and compositions containing an attenuated *L. monocytogenes* prsA2 htrA deletion mutant for use in the presentation of foreign or exogenous antigens and in the treatment or prevention of diseases such as cancer or infectious disease are provided.

4 Claims, 2 Drawing Sheets

(56) References Cited

OTHER PUBLICATIONS

Gründling et al. "Requirement of the *Listeria monocytogenes* Broad-Range Phospholipase PC-PLC during Infection of Human Epithelial Cells" Journal of Bacteriology 2003 185(21):6295-6307.

Henry et al. "Cytolysin-Dependent Delay of Vacuole Maturation in Macrophages Infected with *Listeria monocytogenes*" Cellular Microbiology 2006 8(1):107-119.

Hyyryläinen et al. "A Novel Two-Component Regulatory System in *Bacillus subtilis* for the Survival of Severe Secretion Stress" Molecular Microbiology 2001 41(5):1159-1172.

Ireton, K. "Entry of the Bacterial Pathogen *Listeria monocytogenes* into Mammalian Cells" Cellular Microbiology 2007 9(6):1365-1375.

Johnson et al. "Attenuated *Listeria monocytogenes* monocytogenes Vaccine Vectors Expressing Influenza A Nucleoprotein: Preclinical Evaluation and Oral Inoculation of Volunteers" Microbiology and Immunology 2011 55:304-317.

Kim et al. "*Listeria monocytogenes* $\sigma^B$ Contributes to Invasion of Human Intestinal Epithelial Cells" Infection and Immunity 2004 72(12):7374-7378.

Kim et al. "$\sigma^B$ Contributes to *Listeria monocytogenes* Invasion by Controlling Expression of inlA and in1B" Microbiology 2005 151:3215-3222.

Kocks et al. "L. monocytogenes-Induced Actin Assembly Requires the actA Gene Product, a Surface Protein" Cell 1992 68:521-531.

Lingnau et al. "Expression of the *Listeria monocytogenes* EGD inlA and inlB Genes, Whose Products Mediate Bacterial Entry into Tissue Culture Cell Lines, by PrfA-Dependent and -Independent Mechanisms" Infection and Immunity 1995 63(10):3896-3903.

Marlovits, T. C. and Stebbins, C. E. "Type III Secretion Systems Shape Up as They Ship Out" Current Opinion in Microbiology 2010 13:47-52.

Marquis, H. and Hager, E. J. "pH-Regulated Activation and Release of a Bacteria-Associated Phospholipase C during Intracellular Infection by *Listeria monocytogenes*" Molecular Microbiology 2000 35(2):289-298.

Mathew et al. "Identification of Murine Poxvirus-Specific CD8[+] CTL Epitopes with Distinct Functional Profiles" The Journal of Immunology 2005 174:2212-2219.

Pizarro-Cerdá, J. and Cossart, P. "Subversion of Cellular Functions by *Listeria monocytogenes*" Journal of Pathology 2006 208:215-223.

Port, G. C. and Freitag, N. E. "Identification of Novel *Listeria monocytogenes* Secreted Virulence Factors Following Mutational Activation of the Central Virulence Regulator, PrfA" Infection and Immunity 2007 75(12):5886-5897.

Russel, M. "Macromolecular Assembly and Secretion Across the Bacterial Cell Envelope: Type II Protein Secretion Systems" The Journal of Molecular Biology 1998 279:485-499.

Sarvas et al. "Post-Translocational Folding of Secretory Proteins in Gram-Positive Bacteria" Biochimica et Biophysica Acta 2004 1694:311-327.

Schnupf et al. "Listeriolysin O Secreted by *Listeria monocytogenes* into the Host Cell Cytosol Is Degraded by the N-End Rule Pathway" Infection and Immunity 2007 75(11):5135-5147.

Schnupf et al. "Regulated Translation of Listeriolysin O Controls Virulence of *Listeria monocytogenes*" Molecular Microbiology 2006 61(4):999-1012.

Schnupf, P. and Portnoy, D. A. "Listeriolysin O: a Phagosome-Specific Lysin" Microbes and Infection 2007 9:1176-1187.

Scortti et al. "The PrfA Virulence Regulon" Microbes and Infection 2007 9:1196-1207.

Seveau et al. "Molecular Mechanisms Exploited by *Listeria monocytogenes* during Host Cell Invasion" Microbes and Infection 2007 9:1167-1175.

Skoble et al. "Pivotal Role of VASP in Arp2/3 Complex-Mediated Actin Nucleation, Actin Branch-Formation, and *Listeria monocytogenes* Motility" The Journal of Cell Biology 2001 155(1):89-100.

Skoble et al. "Three Regions within ActA Promote Arp2/3 Complex-Mediated Actin Nucleation and *Listeria monocytogenes* Motility" The Journal of Cell Biology 2000 150(3):527-537.

Smith, G. A. and Portnoy, D. A. "How the *Listeria monocytogenes* ActA Protein Converts Actin Polymerization into a Motile Force" Trends in Microbiology 7997 5(7):272-276.

Stack et al. "Role for HtrA in Stress Induction and Virulence Potential in *Listeria monocytogenes*" Applied and Environmental Microbiology 2005 71(8):4241-4247.

Vazquez-Boland et al. "Nucleotide Sequence of the Lecithinase Operon of *Listeria monocytogenes* and Possible Role of Lecithinase in Cell-to-Cell Spread" Infection and Immunity 1992 60(1):219-230.

Vicente et al. "Penicillin-Binding Protein 3 of *Listeria monocytogenes* as the Primary Lethal Target for β-Lactams" Antimicrobial Agents and Chemotherapy 1990 34(4):539-542.

Wahlström et al. "The Extracytoplasmic Folding Factor PrsA Is Required for Protein Secretion Only in the Presence of the Cell Wall in *Bacillus subtilis*" Microbiology 2003 149:569-577.

Weidenmaier, C. and Peschel, A. "Teichoic Acids and Related Cell-Wall Glycopolymers in Gram-Positive Physiology and Host Interactions" Nature 2008 6:276-287.

Wong et al. "Evidence Implicating the 5' Untranslated Region of *Listeria monocytogenes* actA in the Regulation of Bacterial Actin-Based Motility" Cellular Microbiology 2004 6(2):155-166.

Yeung et al. "Compartmentalization of the Broad-Range Phospholipase C Activity to the Spreading Vacuole Is Critical for *Listeria monocytogenes* Virulence" Infection and Immunity 2007 75(1):44-51.

Young et al. "A New Pathway for the Secretion of Virulence Factors by Bacteria: the Flagellar Export Apparatus Functions as a Protein-Secretion System" Proceedings of the National Academy of Sciences USA 1999 96:6456-6461.

Zemansky et al. "Development of a Mariner-Based Transposon and Identification of *Listeria monocytogenes* Determinants, Including the Peptidyl-Prolyl Isomerase PrsA2, that Contribute to Its Hemolytic Phenotype" Journal of Bacteriology 2009 191(12):3950-3964.

* cited by examiner

ATTENUATED *LISTERIA MONOCYTOGENES* MUTANT AS A VACCINE VECTOR FOR THE DELIVERY OF EXOGENEOUS ANTIGENS

INTRODUCTION

This application claims benefit of priority to U.S. Provisional Application Ser. No. 61/976,144, filed Apr. 7, 2014, the content of which is incorporated herein by reference in its entirety.

This invention was made with government support under grant numbers AI083241 and GM103500 awarded by the National Institutes of Health. The government has certain rights in the invention.

BACKGROUND

During the course of infection, bacterial pathogens are dependent upon the secretion of multiple protein products that modulate host cell physiology and facilitate bacterial growth. A number of protein secretion systems have been identified and functionally characterized for gram-negative bacteria for which the existence of both an inner and outer membrane presents a significant barrier to protein translocation (Cascales (2008) *EMBO Rep.* 9:735-41; Desvaux, et al. (2009) *Trends Microbiol.* 17:139-145; Donnenberg (2000) *Nature* 406:768-74; Gerlach & Hensel (2007) *Int. J. Med. Microbiol.* 297:401-15; Marlovits (2009) *Curr. Opin. Microbiol.* 13:47-52; Russel (1998) *J. Mol. Biol.* 279:485-99; Young, et al. (1999) *Proc. Natl. Acad. Sci. USA* 96:6456-61). In gram-positive bacteria, secreted proteins are translocated across the single bacterial cell membrane in an unfolded state and delivered to the compartment existing between the membrane and the cell wall (Sarvas, et al. (2004) *Biochim. Biophys. Acta* 1694:311-27). The cell walls of gram-positive bacteria are composed of a thick matrix of peptidoglycan layers and glycopolymers, including teichoic acids and lipoteichoic acids (Weidenmaier & Peschel (2008) *Nat. Rev. Microbiol.* 6:276-87), and these abundant anionic polymers have a high capacity to bind divalent metal ions and cationic molecules (Beveridge & Murray (1980) *J. Bacteriol.* 141:876-887; Wahlstrom, et al. (2003) *Microbiology* 149:569-77). Proteins that are translocated across the bacterial membrane therefore enter a challenging environment for protein folding based on the high density of negative charge, high concentrations of cations, and low pH (Sarvas, et al. (2004) *Biochim. Biophys. Acta* 1694:311-27; Wahlstrom, et al. (2003) *Microbiology* 149:569-77). Within this environment, secreted proteins may additionally require further posttranslational modification, proteolytic activation, or sequestration prior to release for interaction with host cell targets. It should be noted that not all secreted proteins are found in the extracellular milieu, as many are specifically localized at the membrane or within the cell wall. Proteins present in bacterial culture supernatants thus constitute a group of exoproteins to which numerous pathogenic traits can be attributed (Desvaux, et al. (2009) *Trends Microbiol.* 17:139-145).

For the facultative intracellular pathogen *Listeria monocytogenes*, protein secretion has been reported to occur primarily via the Sec-mediated secretion pathway (Desvaux & Hebraud (2006) *FEMS Microbiol. Rev.* 30:774-805). Proteins secreted via Sec-dependent secretion include well-characterized virulence factors, such as the internalins InlA and InlB, which mediate host cell invasion (Bierne, et al. (2007) *Microbes Infect.* 9:1156-66; Gaillard, et al. (1991) *Cell* 65:1127-41; Ireton (2007) *Cell Microbiol.* 9:1365-75; Kim, et al. (2004) *Infect. Immun.* 72:7374-78; Kim et al. (2005) *Microbiology* 151:3215-222; Lingnau, et al. (1995) *Infect. Immun.* 63:3896-903; Pizarro-Cerda & Cossart (2006) *J. Pathol.* 208:215-223; Seveau, et al. (2007) *Microbes Infect.* 9:1167-75), listeriolysin-O (LLO) and the broad-range phosphatidyl-choline phospholipase (PC-PLC), which mediate vacuole membrane lysis (Dramsi & Cossart (2003) *Infect. Immun.* 71:3614-8; Glomski, et al. (2003) *Infect. Immun.* 63:3896-903; Glomski, et al. (2002) *J. Cell Biol.* 156:1029-38; Grundling, et al. (2003) *J. Bacteriol.* 185:6295-307; Henry, et al. (2006) *Cell. Microbiol.* 8:107-19; Marquis & Hager (2000) *Mol. Microbiol.* 35:289-98; Schnupf, et al. (2006) *Mol. Microbiol.* 61:999-1012; Schnupf & Portnoy (2007) *Microbes Infect.* 9:1176-87; Schnupf, et al. (2007) *Infect. Immun.* 75:5135-47; Vazquez-Boland, et al. (1992) *Infect. Immun.* 60:219-230; Yeung, et al. (2007) *Infect. Immun.* 75:44-51), and the surface protein ActA, which mediates actin polymerization and cell-to-cell spread within the host (Auerbuch, et al. (2001) *J. Biol. Chem.* 281:31812-22; Boujemaa-Paterski, et al. (2001) *Biochemistry* 40:11390-404; Domann, et al. (1992) *EMBO J.* 11:1981-90; Kocks, et al. (1992) *Cell* 68:521-31; Skoble, et al. (2001) *J. Cell Biol.* 155:89-100; Skoble, et al. (2000) *J. Cell Biol.* 150:527-38; Smith & Portnoy (1997) *Trends Microbiol.* 5:272-6; Wong, et al. (2004) *Cell Microbiol.* 6:155-66). These proteins are critical for the establishment of the *L. monocytogenes* replication niche within the cytosol of infected host cells (Freitag (2006) *Future Microbiol.* 1:89-101; Gray, et al. (2006) *Infect. Immun.* 74:2505-12; Scortti, et al. (2007) *Microbiol. Infect.* 9:1196-1207; Vazquez-Boland, et al. (1990) *Antimicrob. Agents Chemother.* 34:539-42).

*L. monocytogenes* PrsA1 and PrsA2 are secreted proteins that are predicted to function as parvulin-type peptidyl-prolyl isomerase (PPIase) chaperones at the bacterial membrane-cell wall interface to assist in the folding and stability of secreted proteins (Alonzo, III et al. (2009) *Infect. Immun.* 77:2612-23). PrsA2 appears to be primarily adapted for *L. monocytogenes* pathogenesis, based on the regulation of prsA2 expression by the central virulence transcriptional activator PrfA and on the essential requirement for PrsA2 for bacterial virulence in mice (Alonzo, III et al. (2009) *Infect. Immun.* 77:2612-23; Port & Freitag (2007) *Infect. Immun.* 75:5886-97; Zemansky, et al. (2009) *J. Bacteriol.* 191:3950-64). The loss of PrsA2 dramatically reduces bacterial cell-to-cell spread in monolayers of mouse fibroblast cells and also reduces LLO stability and impedes the processing of PC-PLC to its enzymatically active form (Alonzo, III et al. (2009) *Infect. Immun.* 77:2612-23; Chatterjee, et al. (2006) *Infect. Immun.* 74:1323-38; Zemansky, et al. (2009) *J. Bacteriol.* 191:3950-64). Further, it has been demonstrated that prsA2 deletion mutants are defective for bacterial flagellum-mediated swimming motility, an observation that suggests multiple roles for PrsA2 both inside and outside infected host cells (Zemansky, et al. (2009) *J. Bacteriol.* 191:3950-64). In contrast to its homologue in *Bacillus subtilis*, PrsA2 is not required for *L. monocytogenes* viability, and LprsA2 mutants replicate very similarly to wild-type strains in broth culture and on agar medium (Alonzo, III et al. (2009) *Infect. Immun.* 77:2612-23; Sarvas, et al. (2004) *Biochim. Biophys. Acta* 1694:311-27).

Unlike *L. monocytogenes* LprsA2 mutants, strains lacking prsA1 are fully virulent in mouse models of infection (Alonzo, III et al. (2009) *Infect. Immun.* 77:2612-23). prsA1 is not required for bacterial growth in broth culture, and its potential contributions to other aspects of *L. monocytogenes* physiology are as yet undefined. PrsA2 and PrsA1 are highly similar at the amino acid sequence level; thus, it is possible that PrsA2 and PrsA1 share some degree of functional overlap (Alonzo, III et al. (2009) Infect. Immun. 77:2612-23). In *B. subtilis,* the depletion of PrsA leads to the induction of the CssR/S two-component system and increased expression of the HtrA chaperone/protease in response to the accumulation of misfolded proteins at the bacterial membrane-cell wall interface (Hyyrylainen, et al. (2001) *Mol. Microbiol.* 41:1159-72; Sarvas, et al. (2004) *Biochim. Biophys. Acta* 1694:311-27). The loss or depletion of both PrsA2 and PrsA1 in *L. monocytogenes* could potentially elicit a similar membrane stress response if one or both are required for the folding of a large number of secreted proteins.

Initially characterized in *Escherichia coli,* HtrA is one of several proteins, collectively known as heat shock proteins, whose expression is essential for survival of bacteria at high temperatures. In addition, htrA has been shown to be essential for the pathogenicity of several gram-negative and gram-positive bacteria, namely, *Salmonella enterica* serovar *Typhimurium, Klebsiella pneumoniae, Streptococcus pyogenes,* and *Streptococcus pneumonia,* as well as the antibiotic stress response in *Lactococcus lactis* and *Staphylococcus aureus.* Analysis of HtrA in listerial pathogenesis revealed a ~1-log reduction in the level of the htrA mutant relative to the wild-type 3 days after intraperitoneal infection (Stack, et al. (2005) *Appl. Environ. Microbiol.* 71:4241-7). Likewise, the survival of a htrA prsA2 double mutant has been shown to be significantly impaired in mice (Alonzo, III & Freitag (2010) *Infect. Immun.* 70(11):4944-4257).

*L. monocytogenes* has been shown to exhibit the ability to induce an innate immune response that leads to robust and highly functional CD4 and CD8 T cell immunity specific for vaccine-encoded antigens. see, e.g., US 2003/0202985; US 2002/0136737; Angelakopoulos, et al. (2002) *Infect. Immun.* 70:3592-601; Johnson, et al. (2011) *Microbiol. Immunol.* 55:304-17; Mathew, et al. (2005) *J. Immunol.* 174:2212-9; and Radulovic, et al. (2009) *J. Buon.* 14:(suppl. 1):S165-8.

SUMMARY OF THE INVENTION

This invention provides a vaccine containing an attenuated *Listeria monocytogenes* prsA2 htrA deletion mutant and a carrier. In some embodiments, the mutant further includes in its genome one or more nucleic acid molecules encoding exogenous antigens, e.g., bacterial, viral, fungal, parasitic or tumor antigens. Methods for using such vaccines to elicit an immune response or prevent or treat cancer or an infection are also provided as is a composition containing a pharmaceutically acceptable carrier and an attenuated *Listeria monocytogenes* prsA2 htrA deletion mutant optionally including in its genome one or more nucleic acid molecules encoding exogenous antigens.

DETAILED DESCRIPTION OF THE INVENTION

Figure 1A:
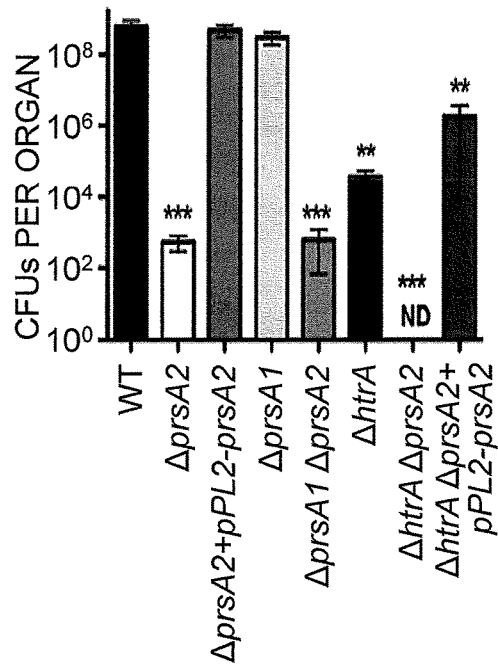
FIGS. 1A and 1B show that *L. monocytogenes* prsA2 htrA deletion mutant is highly attenuated. Mice were injected through the tail vein with $2\times10^4$ colony forming units (CFU) of each *L. monocytogenes* strain. The livers (FIG. 1A) and spleens (FIG. 1B) of infected mice were recovered 72 hours post-infection (hpi) and the bacterial burden in each organ was determined. A minimum of 5 mice per group were used, and the means and standard deviations are shown.

It has now been found that a *L. monocytogenes* prsA2 htrA deletion mutant reaches the cytosol of infected host cells to deliver antigen. However, the bacterium is defective for intracellular replication and rapidly loses viability within infected cells. Despite this loss in viability, the htrA prsA2 double deletion strain is able to elicit robust T cell-dependent immune responses and confer protection to subsequent *L. monocytogenes* infection. The greater than 100,000-fold level of attenuation combined with the ability to invade and gain access to the mammalian cell cytosol indicates that the htrA prsA2 double deletion strain is a safe and effective vaccine vector delivery vehicle. Therefore, the present invention provides vaccines and compositions containing the *L. monocytogenes* prsA2 htrA deletion mutant for use in the presentation of foreign or exogenous antigens and in the treatment or prevention of diseases such as cancer or infectious disease.

The attenuated *L. monocytogenes* htrA prsA2 double deletion of this invention has been developed to address the need for safe and immunologically potent *L. monocytogenes*-based vaccine platforms. Indeed, when compared to a conventional actA mutant, which is approximately 1000-fold less virulent than wild-type *L. monocytogenes,* the instant htrA prsA2 double deletion mutant is more highly attenuated for virulence (10,000 to 100,000-fold less virulent than wild-type *L. monocytyogenes*). The attenuated *L. monocytogenes* htrA prsA2 double deletion mutant of this invention is therefore of use in a vaccine for expressing one or more antigens of interest and stimulating robust host immune responses that mediate protective immunity.

For the purposes of this invention, a "vaccine" encompasses preventative vaccines. Vaccine also encompasses therapeutic vaccines, e.g., a vaccine administered to a mammal having a condition or disorder associated with the antigen or epitope provided by the vaccine. The attenuated *L. monocytogenes* htrA prsA2 double deletion mutant may be used to deliver a polypeptide described herein to antigen-presenting cells in the host organism. As described herein, *L. monocytogenes* provides a preferred vaccine platform for expression of the antigens of the present invention.

"Attenuation" and "attenuated" means that the *L. monocytogenes* is modified to reduce toxicity to a host. The host can be a human or animal host, or an organ, tissue, or cell. Attenuation can be assessed by measuring, e.g., an indicum or indicia of toxicity, the $LD_{50}$, the rate of clearance from an organ, and/or the competitive index (see, e.g., Auerbuch, et al. (2001) *Infect. Immunity* 69:5953-5957). Generally, an attenuated mutant results in an increase in the $LD_{50}$ and/or an increase in the rate of clearance by at least 25%; more generally by at least 50%; most generally by at least 100% (2-fold); normally by at least 5-fold; more normally by at least 10-fold; most normally by at least 50-fold; often by at least 100-fold; more often by at least 500-fold; and most often by at least 1000-fold; usually by at least 5000-fold; more usually by at least 10,000-fold; and most usually by at least 50,000-fold; and most often by at least 100,000-fold.

The attenuated *L. monocytogenes* mutant exemplified herein is a double deletion mutant of the htrA prsA2 genes. In particular embodiments, the double deletion mutant is loss-of-function mutant, with abolished protein function. The sequence of htrA gene is known in the art an available under GENBANK Accession No. AY049084. Likewise, the prsA2 gene is known and available under Gene ID BN389_22520 or at chromosomal location 2301560-2302441 of GENBANK Accession No. HF558398. The htrA prsA2 genes can be mutated by any conventional method in the art including, but not limited to, in-frame deletion based on homologous recombination (Camilli, et al. (1993) *Mol. Microbiol.* 8:143-57), targeted disruption using site-specific recombinases such as the Cre-lox system (Lambert, et al. (2007) *Appl. Environ. Microbiol.* 73:1126-35) or FLP recombinase and frt sites, or targeted insertional disruption using, e.g., the TARGETRON gene knockout system, which inserts a mobile group II intron into the gene of interest (Sigma, St. Louis, Mo.). By way of illustration, an in-frame deletion mutant is constructed by PCR amplifying upstream and downstream sequences flanking the open reading frame of interest using *L. monocytogenes* chromosomal DNA as template. The PCR products are subsequently digested with appropriate enzymes and ligated to form a ΔORF insert to knock out the gene of interest by homologous recombination. The insert is amplified by PCR, cloned into a plasmid, and screened for the presence of the insert. DNA of the plasmid containing the insert is introduced into *L. monocytogenes*, and plasmid integration and excision are performed according to established methods (Schaferkordt & Chakraborty (1995) *BioTechniques* 19:720-2).

Targeted disruption or deletion of the htrA and prsA2 genes results in bacterial cell death in infected cells, as compared to its isogenic parent *Listeria* strain. Thus, the elimination of htrA and prsA2 can be assessed by comparing the virulence or toxicity mediated by the mutated genes with that mediated by the non-mutated (or parent) gene. "Mutated gene" encompasses deletions, point mutations, and frameshift mutations in regulatory regions of the gene, coding regions of the gene, non-coding regions of the gene, or any combination thereof.

A vaccine containing an attenuated *L. monocytogenes* htrA prsA2 double deletion mutant can be administered to a host, either alone or in combination with a carrier. A "carrier" of use in a vaccine is meant to include, but is not limited to, sterile distilled water, saline, phosphate buffered solutions or bicarbonate buffered solutions. The vaccines of the present invention can be stored, e.g., frozen, lyophilized, as a suspension, as a cell paste, or complexed with a solid matrix or gel matrix.

A preferred use of the attenuated *L. monocytogenes* htrA prsA2 double deletion mutant described herein is as a vaccine platform for initiating both an innate immune response as well as an antigen-specific T cell response against a recombinantly expressed antigen(s). For example, *L. monocytogenes* expressing the antigen(s) described herein can stimulate robust dendritic cell activation, robust host immune responses that can mediate robust protective immunity. In response to this immune stimulation, NK cells and antigen presenting cells (APCs) are recruited to the liver following intravenous vaccination routes, or, alternatively to the vaccination site following other routes of vaccination, for example, by intramuscular, subcutaneous, oral, or intradermal immunization routes. In certain embodiments, the vaccine platform of the present invention induces a CD4+ and/or CD8+ antigen-specific T cell response against one or more antigens expressed by the vaccine platform.

The ability of *L. monocytogenes* to serve as a vaccine vector has been reviewed in Wesikirch, et al. (1997) *Immunol. Rev.* 158:159-169. A number of desirable features of the natural biology of *L. monocytogenes* make it an attractive platform for application to a therapeutic vaccine. The central rationale is that the intracellular lifecycle of *L. monocytogenes* enables effective stimulation of CD4+ and CD8+ T cell immunity. Multiple pathogen associated molecular pattern (PAMP) receptors including TLRs (TLR2, TLR5, TLR9) nucleotide-binding oligomerization domains (NOD), and Stimulator of Interferon Genes (STING) are triggered in response to interaction with *L. monocytogenes* macromolecules upon infection, resulting in the pan-activation of innate immune effectors and release of Th-1 polarizing cytokines, exerting a profound impact on the development of a CD4+ and CD8+ T cell response against the expressed antigens.

Strains of *L. monocytogenes* have recently been developed as effective intracellular delivery vehicles of heterologous proteins providing delivery of antigens to the immune system to induce an immune response to clinical conditions that do not permit injection of the disease-causing agent, such as cancer and HIV. See, e.g., U.S. Pat. No. 6,051,237; Gunn, et al. (2001) *J. Immunol.* 167:6471-6479; Liau, et al. (2002) *Cancer Res.* 62:2287-2293; U.S. Pat. No. 6,099,848; WO 99/25376; WO 96/14087; and U.S. Pat. No. 5,830,702). A recombinant *L. monocytogenes* vaccine expressing a lymphocytic choriomeningitis virus (LCMV) antigen has also been shown to induce protective cell-mediated immunity to the antigen (Shen, et al. (1995) *Proc. Natl. Acad. Sci. USA* 92:3987-3991.

Accordingly, in certain embodiments, the attenuated *L. monocytogenes* htrA prsA2 double deletion mutant of the invention contains, in its genome, one or more nucleic acid molecules encoding exogenous antigens. The antigen(s) are preferably under the control of bacterial expression sequences and are stably integrated into the *L. monocytogenes* genome. An antigen is exogenous in the sense that it is not naturally expressed by *L. monocytogenes*.

In some embodiments, the exogenous antigen is a tumor antigen. Examples of exogenous tumor antigens that may find use in the invention are listed in Table 1.

TABLE 1

| Tumor antigens | Reference |
| --- | --- |
| Mesothelin | GENBANK Accession No. NM_005823; Hassan, et al. (2004) *Clin. Cancer Res.* 10: 3937-3942; Muminova, et al. (2004) *BMC Cancer* 4: 19; Iacobuzio-Donahue, et al. (2003) *Cancer Res.* 63: 8614-8622). |
| Wilms' tumor-1 associated protein (Wt-1), including isoforms A-D. | WT-1 isoform A (GENBANK Acc. Nos. NM_000378 and NP_000369). WT-1 isoform B (GENBANK Acc. Nos. NM_024424 and NP_077742). WT-1 isoform C (GENBANK Acc. Nos. NM_024425; NP_077743). WT-1 isoform D (GENBANK Acc. Nos. NM_024426; NP_077744) |
| Stratum corneum chymotryptic enzyme(SCCE), and variants thereof. | GENBANK Acc. No. NM_005046; NM_139277; AF332583. See also, e.g., Bondurant, et al. (2005) *Clin. Cancer Res.* 11: 3446-3454; Santin et al. (2004) *Gynecol. Oncol.* 94: 283-288; Shigemasa, et al. (2001) *Int. J. Gynecol. Cancer* 11: 454-461; Sepehr, et al. (2001) *Oncogene* 20: 7368-7374. |
| MHC class I chain-related protein A (MICA); MHC class I chain-related protein B (MICB). | See, e.g., Groh, et al. (2005) *Proc. Natl. Acad. Sci. USA* 102: 6461-6466; GENBANK Acc. Nos. NM_000247; BC_016929; AY750850; NM_005931. |
| Gastrin and peptides derived from gastrin; gastrin/CCK-2 receptor (also known as CCK-B). | Harris, et al. (2004) *Cancer Res.* 64: 5624-5631; Gilliam, et al. (2004) *Eur. J. Surg. Oncol.* 30: 536-543; Laheru & Jaffee (2005) *Nature Rev. Cancer* 5: 459-467. |
| Glypican-3 (an antigen of, e.g., hepatocellular carcinoma and melanoma). | GENBANK Acc. No. NM_004484. Nakatsura, et al. (2003) *Biochem. Biophys. Res. Commun.* 306: 16-25; Capurro, et al. (2003) *Gasteroenterol.* 125: 89-97; Nakatsura, et al. (2004) *Clin. Cancer Res.* 10: 6612-6621). |
| Coactosin-like protein. | Nakatsura, et al. (2002) *Eur. J. Immunol.* 32: 826-836; Laheru & Jaffee (2005) *Nature Rev. Cancer* 5: 459-467. |
| Prostate stem cell antigen (PSCA). | GENBANK Acc. No. AF043498; AR026974; AR302232 (see also, e.g., Argani, et al. (2001) *Cancer Res.* 61: 4320-4324; Christiansen, et al. (2003) *Prostate* 55: 9-19). |
| Prostate acid phosphatase (PAP); | Small, et al. (2000) *J. Clin. Oncol.* 18: 3894-3903; Altwein & Luboldt (1999) *Urol. Int.* 63: 62-71; Chan, et al. (1999) *Prostate* 41: 99-109; |
| Prostate-specific antigen (PSA); PSM; PSMA. | Ito, et al. (2005) Cancer 103: 242-250; Schmittgen, et al. (2003) *Int. J. Cancer* 107: 323-329; Millon, et al. (1999) *Eur. Urol.* 36: 278-285. |
| Six-transmembrane epithelial antigen of prostate (STEAP). | See, e.g., Machlenkin, et al. (2005) *Cancer Res.* 65: 6435-6442; GENBANK Acc. No. NM_018234; NM_001008410; NM_182915; NM_024636; NM_012449; BC0110802. |
| Prostate carcinoma tumor antigen-1 (PCTA-1). | See, e.g., Machlenkin, et al. (2005) *Cancer Res.* 65: 6435-6442; GenBank Acc. No. L78132. |
| Prostate tumor-inducing gene-1 (PTI-1). | See, e.g., Machlenkin, et al. (2005) *Cancer Res.* 65: 6435-6442). |
| Prostate-specific gene with homology to G protein-coupled receptor. | See, e.g., Machlenkin, et al. (2005) *Cancer Res.* 65: 6435-6442). |
| Prostase (an antrogen regulated serine protease). | See, e.g., Machlenkin, et al. (2005) *Cancer Res.* 65: 6435-6442; GENBANK Acc. No. BC096178; BC096176; BC096175. |
| Proteinase 3. | GENBANK Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. | GENBANK Acc. No. NM_001327 (NY-ESO-1) (see also, e.g., Li, et al. (2005) *Clin. Cancer Res.* 11: 1809-1814; Chen, et al. (2004) *Proc. Natl. Acad. Sci. USA* 101(25): 9363-9368; Kubuschok, et al. (2004) *Int. J. Cancer.* 109: 568-575; Scanlan, et al. (2004) *Cancer Immun.* 4: 1; Scanlan, et al. (2002) *Cancer Res.* |

TABLE 1-continued

| Tumor antigens | Reference |
|---|---|
| | 62: 4041-4047; Scanlan, et al. (2000) *Cancer Lett.* 150: 155-164; Dalerba, et al. (2001) *Int. J. Cancer* 93: 85-90; Ries, et al. (2005) *Int. J. Oncol.* 26: 817-824. |
| MAGE-A1; MAGE-A2; MAGE-A3; MAGE-A4; MAGE-A6; MAGE-A9; MAGE-A10; MAGE-A12; GAGE-3/6; NT-SAR-35; BAGE; CA125. | Otte, et al. (2001) *Cancer Res.* 61: 6682-6687; Lee, et al. (2003) *Proc. Natl. Acad. Sci. USA* 100: 2651-2656; Sarcevic, et al. (2003) *Oncology* 64: 443-449; Lin, et al. (2004) *Clin. Cancer Res.* 10: 5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) *Cancer Res.* 59: 3157-3165; Scarcella, et al. (1999) *Clin. Cancer Res.* 5: 335-341. |
| HIP1R; LMNA; KIAA1416; Seb4D; KNSL6; TRIP4; MBD2; HCAC5; MAGEA3. | Scanlan, et al. (2002) *Cancer Res.* 62: 4041-4047. |
| DAM family of genes, e.g., DAM-1; DAM-6. | Fleishhauer, et al. (1998) *Cancer Res.* 58: 2969-2972. |
| RCAS1. | Enjoji, et al. (2004) *Dig. Dis. Sci.* 49: 1654-1656. |
| RU2. | Van Den Eynde, et al. (1999) *J. Exp. Med.* 190: 1793-1800. |
| CAMEL. | Slager, et al. (2004) *J. Immunol.* 172: 5095-5102; Slager, et al. (2004) *Cancer Gene Ther.* 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP; NY-CO-4; NY-CO-95/KIAA1416; KNSL6; seb4D. | Scanlan, et al. (2002) *Cancer Res.* 62: 4041-4047. |
| N-Acetyl glucosaminyl-tranferase V (GnT-V). | Dosaka-Akita, et al. (2004) *Clin. Cancer Res.* 10: 1773-1779. |
| Elongation factor 2 mutated (ELF2M). | Renkvist, et al. (2001) *Cancer Immunol Immunother.* 50: 3-15. |
| HOM-MEL-40/SSX2; BRDT. | Neumann, et al. (2004) *Int. J. Cancer* 112: 661-668; Scanlan, et al. (2000) *Cancer Lett.* 150: 155-164. Scanlan, et al. (2000) *Cancer Lett.* 150: 155-164. |
| SAGE; HAGE. | Sasaki, et al. (2003) *Eur. J. Surg. Oncol.* 29: 900-903. |
| RAGE. | See, e.g., Li, et al. (2004) *Am. J. Pathol.* 164: 1389-1397; Shirasawa, et al. (2004) *Genes to Cells* 9: 165-174. |
| MUM-1 (melanoma ubiquitous mutated); MUM-2; MUM-2 Arg-Gly mutation; MUM-3. | Gueguen, et al. (1998) *J. Immunol.* 160: 6188-6194; Hirose, et al. (2005) *Int. J. Hematol.* 81: 48-57; Baurain, et al. (2000) *J. Immunol.* 164: 6057-6066; Chiari, et al. (1999) *Cancer Res.* 59: 5785-5792. |
| LDLR/FUT fusion protein antigen of melanoma. | Wang, et al. (1999) *J. Exp. Med.* 189: 1659-1667. |
| NY-REN series of renal cancer antigens. | Scanlan, et al. (2002) *Cancer Res.* 62: 4041-4047; Scanlan, et al. (1999) *Cancer Res.* 83: 456-464. |
| NY-BR series of breast cancer antigens, e.g., NY-BR-62; NY-BR-75; NY-BR-85; NY-BR-62; NY-BR-85. | Scanlan, et al. (2002) *Cancer Res.* 62: 4041-4047; Scanlan, et al. (2001) *Cancer Immunity* 1: 4. |

TABLE 1-continued

| Tumor antigens | Reference |
| --- | --- |
| BRCA-1; BRCA-2. | Stolier, et al. (2004) *Breast J.* 10: 475-480; Nicoletto, et al. (2001) *Cancer Treat Rev.* 27: 295-304. |
| DEK/CAN fusion protein. | Von Lindern, et al. (1992) *Mol. Cell. Biol.* 12: 1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GENBANK Acc. Nos. P01112; P01116; M54969; M54968; P01111; P01112; K00654. See also, e.g., GENBANK Acc. Nos. M26261; M34904; K01519; K01520; BC006499; NM_006270; NM_002890; NM_004985; NM_033360; NM_176795; NM_005343. |
| BRAF (an isoform of RAF). | Tannapfel, et al. (2005) *Am. J. Clin. Pathol.* 123: 256-2601; Tsao & Sober (2005) *Dermatol. Clin.* 23: 323-333. |
| Melanoma antigens, including HST-2 melanoma cell antigens. | GENBANK Acc. No. NM_206956; NM_206955; NM_206954; NM_206953; NM_006115; NM_005367; NM_004988; AY148486; U10340; U10339; M77481. See, e.g., Suzuki, et al. (1999) *J. Immunol.* 163: 2783-2791. |
| Survivin | GENBANK Acc. No. AB028869; U75285 (see also, e.g., Tsuruma, et al. (2004) *J. Translational Med.* 2: 19; Pisarev, et al. (2003) *Clin. Cancer Res.* 9: 6523-6533; Siegel, et al. (2003) *Br. J. Haematol.* 122: 911-914; Andersen, et al. (2002) *Histol. Histopathol.* 17: 669-675). |
| MDM-2 | NM_002392; NM_006878 (see also, e.g., Mayo, et al. (1997) *Cancer Res.* 57: 5013-5016; Demidenko & Blagosklonny (2004) *Cancer Res.* 64: 3653-3660). |
| Methyl-CpG-binding proteins (MeCP2; MBD2). | Muller, et al. (2003) *Br. J. Cancer* 89: 1934-1939; Fang, et al. (2004) *World J. Gastroenterol.* 10: 3394-3398. |
| NA88-A. | Moreau-Aubry, et al. (2000) *J. Exp. Med.* 191: 1617-1624. |
| Histone deacetylases (HDAC), e.g., HDAC5. | Waltregny, et al. (2004) *Eur. J. Histochem.* 48: 273-290; Scanlan, et al. (2002) *Cancer Res.* 62: 4041-4047. |
| Cyclophilin B (Cyp-B). | Tamura, et al. (2001) *Jpn. J. Cancer Res.* 92: 762-767. |
| CA 15-3; CA 27.29. | Clinton, et al. (2003) *Biomed. Sci. Instrum.* 39: 408-414. |
| Heat shock protein Hsp70. | Faure, et al. (2004) *Int. J. Cancer* 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) *Cancer Res.* 59: 1445-1448. |
| MAGE-A, B, C, and D families. MAGE-B5; MAGE-B6; MAGE-C2; MAGE-C3; MAGE-3; MAGE-6. | Lucas, et al. (2000) *Int. J. Cancer* 87: 55-60; Scanlan, et al. (2001) *Cancer Immun.* 1: 4. |
| Kinesin 2; TATA element modulatory factor 1; tumor protein D52; MAGE D; NY-BR proteins. | Scanlan, et al. (2001) *Cancer Immun.* 30: 1-4. |
| Alpha-fetoprotein (AFP) | Grimm, et al. (2000) *Gastroenterol.* 119: 1104-1112. |
| SART1; SART2; SART3; ART4. | Kumamuru, et al. (2004) *Int. J. Cancer* 108: 686-695; Sasatomi, et al. (2002) *Cancer* 94: 1636-1641; Matsumoto, et al. (1998) *Jpn. J. Cancer Res.* 89: 1292-1295; Tanaka, et al. (2000) *Jpn. J. Cancer Res.* 91: 1177-1184. |
| Preferentially expressed antigen of melanoma (PRAME). | Matsushita, et al. (2003) *Leuk. Lymphoma* 44: 439-444; Oberthuer, et al. (2004) *Clin. Cancer Res.* 10: 4307-4313. |

TABLE 1-continued

| Tumor antigens | Reference |
| --- | --- |
| Carcinoembryonic antigen (CEA), CAP1-6D enhancer agonist peptide. | GENBANK Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis & Cheever (1997) Adv. Cancer Res. 71: 343-371. |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GENBANK Acc. No. NM_001922. (see also, e.g., Bronte, et al. (2000) Cancer Res. 60: 253-258). |
| Gp100/pmel-17. | GENBANK Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infect. Immun. 73: 1939-1946. |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | US 2002/0150588 |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. |

TABLE 1-continued

| Tumor antigens | Reference |
| --- | --- |
| p53; E-cadherin; cyclooxygenase-2 (COX-2). | *Surg. Res.* 120: 242-248; Abutaily, et al. (2003) *J. Pathol.* 201: 355-362; Liang, et al. (2004) *Br. J. Surg.* 91: 355-361; Shirakawa, et al. (2004) *Clin. Cancer Res.* 10: 4342-4348. |
| Renal cell carcinoma antigen bound by mAB G250. | Mulders, et al. (2003) *Urol. Clin. North Am.* 30: 455-465; Steffens, et al. (1999) *AntiCancer Res.* 19: 1197-1200. |
| EphA2 | See, e.g., US 2005/0281783 A1; GENBANK Accession No. NM_004431 (human); GENBANK Accession No. NM_010139 (Mouse); GENBANK Accession No. AB038986 (Chicken, partial sequence); GENBANK Accession Nos. NP_004422, AAH37166, and AAA53375 (human); GENBANK Accession Nos. NP_034269 (mouse), AAH06954 (mouse), XP_345597 (rat), and BAB63910 (chicken). |

In other embodiments, the exogenous antigen is a bacterial, viral, fungal, or parasitic antigen. Examples of exogenous antigens from pathogenic organisms that may find use in the invention are listed in Table 2.

TABLE 2

| Antigen | Reference |
| --- | --- |
| Malarial antigens | |
| Circumsporozoite protein (CSP); SSP2; HEP17; Exp-1 orthologs found in *P. falciparum*; and LSA-1. | See, e.g., Haddad, et al. (2004) *Infect. Immun.* 72: 1594-1602; Hoffman, et al. (1997) *Vaccine* 15: 842-845; CSP (see, e.g., GENBANK Acc. No. AB121024). SSP2 (see, e.g., GENBANK Acc. No. AF249739). LSA-1 (see, e.g., GENBANK Acc. No. Z30319). |
| Ring-infected erythrocyte surface protein (RESA); merozoite surface protein 2 (MSP2); Spf66; merozoite surface protein 1(MSP1); 195A; BVp42. | See, e.g., Stirnadel, et al. (2000) *Int. J. Epidemiol.* 29: 579-586; Krzych, et al. (1995) *J. Immunol.* 155: 4072-4077. See also, Good, et al. (2004) *Immunol. Rev.* 201: 254-267; Good, et al. (2004) *Ann. Rev. Immunol.* 23: 69-99. MSP2 (see, e.g., GENBANK Acc. No. X96399; X96397). MSP1 (see, e.g., GENBANK Acc. No. X03371). RESA (see, e.g., GENBANK Acc. No. X05181; X05182). |
| Apical membrane antigen 1 (AMA1). | See, e.g., Gupta, et al. (2005) *Protein Expr. Purif.* 41: 186-198. AMA1 (see, e.g., GENBANK Acc. No. AJ494905; AJ490565). |
| Viruses and Viral Antigens | |
| Hepatitis A | GENBANK Acc. Nos., e.g., NC_001489; AY644670; X83302; K02990; M14707. |
| Hepatitis B | Complete genome (see, e.g., GENBANK Acc. Nos. AB214516; NC_003977; AB205192; AB205191; AB205190; AJ748098; AB198079; AB198078; AB198076; AB074756). |

TABLE 2-continued

| Antigen | Reference |
| --- | --- |
| Hepatitis C | Complete genome (see, e.g., GENBANK Acc. Nos. NC_004102; AJ238800; AJ238799; AJ132997; AJ132996; AJ000009; D84263). |
| Hepatitis D | GENBANK Acc. Nos, e.g. NC_001653; AB118847; AY261457. |
| Human papillomavirus, including all 200+ subtypes (classed in 16 groups), such as the high risk subtypes 16, 18, 30, 31, 33, 45. | See, e.g., Trimble, et al. (2003) *Vaccine* 21: 4036-4042; Kim, et al. (2004) *Gene Ther.* 11: 1011-1018; Simon, et al. (2003) *Eur. J. Obstet. Gynecol. Reprod. Biol.* 109: 219-223; Jung, et al. (2004) *J. Microbiol.* 42: 255-266; Damasus-Awatai & Freeman-Wang (2003) *Curr. Opin. Obstet. Gynecol.* 15: 473-477; Jansen & Shaw (2004) *Annu. Rev. Med.* 55: 319-331; Roden and Wu (2003) *Expert Rev. Vaccines* 2: 495-516; de Villiers, et al. (2004) *Virology* 324: 17-24; Hussain & Paterson (2005) *Cancer Immunol. Immunother.* 54: 577-586; Molijn, et al. (2005) *J. Clin. Virol.* 32 (Suppl. 1) S43-S51. GENBANK Acc. Nos. AY686584; AY686583; AY686582; NC_006169; NC_006168; NC_006164; NC_001355; NC_001349; NC_005351; NC_001596). |
| Human T-cell lymphotropic virus (HTLV) types I and II, including the HTLV type I subtypes | See, e.g., Capdepont, et al. (2005) *AIDS Res. Hum. Retrovirus* 21: 28-42; Bhigjee, et al. (1999) *AIDS Res. Hum. Restrovirus* 15: 1229-1233; Vandamme, et al. (1998) *J. Virol.* 72: 4327-4340; Vallejo, et al. (1996) *J. Acquir. Immune Defic. Syndr. Hum. Retrovirol.* 13: 384-391. HTLV type I (see, e.g., GENBANK Acc. Nos. AY563954; AY563953. |

TABLE 2-continued

| Antigen | Reference |
|---|---|
| Cosmopolitan, Central African, and Austro-Melanesian, and the HTLV type II subtypes IIa, IIb, IIc, and IId. | HTLV type II (see, e.g., GENBANK Acc. Nos. L03561; Y13051; AF139382). |
| Coronaviridae, including Coronaviruses, such as SARS-coronavirus (SARS-CoV), and Toroviruses. | See, e.g., Brian & Baric (2005) *Curr. Top. Microbiol. Immunol.* 287: 1-30; Gonzalez, et al. (2003) *Arch. Virol.* 148: 2207-2235; Smits, et al. (2003) *J. Virol.* 77: 9567-9577; Jamieson, et al. (1998) *J. Infect. Dis.* 178: 1263-1269 (GENBANK Acc. Nos. AY348314; NC_004718; AY394850). |
| Rubella virus. | GENBANK Acc. Nos. NC_001545; AF435866. |
| Mumps virus, including the genotypes A, C, D, G, H, and I. | See, e.g., Orvell, et al. (2002) *J. Gen. Virol.* 83: 2489-2496. See, e.g., GENBANK Acc. Nos. AY681495; NC_002200; AY685921; AF201473. |
| Coxsackie virus A including the serotypes 1, 11, 13, 15, 17, 18, 19, 20, 21, 22, and 24 (also known as Human enterovirus C; HEV-C). | See, e.g., Brown, et al. (2003) *J. Virol.* 77: 8973-8984. GENBANK Acc. Nos. AY421768; AY790926; X67706. |
| Coxsackie virus B, including subtypes 1-6. | See, e.g., Ahn, et al. (2005) *J. Med. Virol.* 75: 290-294; Patel, et al. (2004) *J. Virol. Methods* 120: 167-172; Rezig, et al. (2004) *J. Med. Virol.* 72: 268-274. GENBANK Acc. No. X05690. |
| Human enteroviruses including, e.g., human enterovirus A (HEV-A, CAV2 to CAV8, CAV10, CAV12, CAV14, CAV16, and EV71) and also including HEV-B (CAV9, CBV1 to CBV6, E1 to E7, E9, E11 to E21, E24 to E27, E29 to E33, and EV69 and E73), as well as HEV. | See, e.g., Oberste, et al. (2004) *J. Virol.* 78: 855-867. Human enterovirus A (GENBANK Acc. Nos. NC_001612); human enterovirus B (NC_001472); human enterovirus C (NC_001428); human enterovirus D (NC_001430). Simian enterovirus A (GENBANK Acc. No. NC_003988). |
| Polioviruses including PV1, PV2, and PV3. | See, e.g., He, et al. (2003) *J. Virol.* 77: 4827-4835; Hahsido, et al. (1999) *Microbiol. Immunol.* 43: 73-77. GENBANK Acc. No. AJ132961 (type 1); AY278550 (type 2); X04468 (type 3). |
| Viral encephalitides viruses, including equine encephalitis, Venezuelan equine encephalitis (VEE) (including subtypes IA, IB, IC, ID, IIIC, IIID), Eastern equine encephalitis (EEE), Western equine encephalitis (WEE), St. Louis encephalitis, Murray Valley (Australian) encephalitis, Japanese encephalitis, and tick-born encephalitis. | See, e.g., Estrada-Franco, et al. (2004) *Emerg. Infect. Dis.* 10: 2113-2121; Das, et al. (2004) *Antiviral Res.* 64: 85-92; Aguilar, et al. (2004) *Emerg. Infect. Dis.* 10: 880-888; Weaver, et al. (2004) *Arch. Virol. Suppl.* 18: 43-64; Weaver, et al. (2004) *Annu. Rev. Entomol.* 49: 141-174. Eastern equine encephalitis (GENBANK Acc. No. NC_003899; AY722102) Western equine encephalitis (NC_003908). |
| Human herpesviruses, including cytomegalovirus (CMV), Epstein-Barr virus (EBV), human herpesvirus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster. virus (VZV) | See, e.g., Studahl, et al. (2000) *Scand. J. Infect. Dis.* 32: 237-248; Padilla, et al. (2003) *J. Med. Virol.* 70 (Suppl. 1) S103-S110; Jainkittivong & Langlais (1998) *Oral Surg. Oral Med.* 85: 399-403. GENBANK Nos. NC_001806 (herpesvirus 1); NC_001798 (herpesvirus 2); X04370 and NC_001348 (herpesvirus 3); NC_001345 (herpesvirus 4); NC_001347 (herpesvirus 5); X83413 and NC_000898 (herpesvirus 6); NC_001716 (herpesvirus 7). Human herpesviruses types 6 and 7 (HHV-6; HHV-7) are disclosed by, e.g., Padilla, et al. (2003) *J. Med. Virol.* 70 (Suppl. 1)S103-S110. Human herpesvirus 8 (HHV-8), including subtypes A-E, are disclosed in, e.g., Treurnicht, et al. (2002) *J. Med. Virol.* 66: 235-240. |
| HIV-1 including group M (including subtypes A to J) and group O (including any distinguishable subtypes) (HIV-2, including subtypes A-E. | See, e.g., Smith, et al. (1998) *J. Med. Virol.* 56: 264-268. See also, e.g., GENBANK Acc. Nos. DQ054367; NC_001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| Epstein-Barr virus (EBV), including subtypes A and B. | See, e.g., Peh, et al. (2002) *Pathology* 34: 446-450. Epstein-Barr virus strain B95-8 (GENBANK Acc. No. V01555). |
| Reovirus, including serotypes and strains 1, 2, and 3, type 1 Lang, type 2 Jones, and type 3 Dearing. | See, e.g., Barthold, et al. (1993) *Lab. Anim. Sci.* 43: 425-430; Roner, et al. (1995) *Proc. Natl. Acad. Sci. USA* 92: 12362-12366; Kedl, et al. (1995) *J. Virol.* 69: 552-559. GENBANK Acc. No. K02739 (sigma-3 gene surface protein). |
| Cytomegalovirus (CMV) subtypes include CMV subtypes I-VII. | See, e.g., Chern, et al. (1998) *J. Infect. Dis.* 178: 1149-1153; Vilas Boas, et al. (2003) *J. Med. Virol.* 71: 404-407; Trincado, et al. (2000) *J. Med. Virol.* 61: 481-487. |
| Rhinovirus, including all serotypes. | GENBANK Acc. No. X17403. Human rhinovirus 2 (GENBANK Acc. No. X02316); Human rhinovirus B (GENBANK Acc. No. NC_001490); Human rhinovirus 89 (GENBANK Acc. No. NC_001617); Human rhinovirus 39 (GENBANK Acc. No. AY751783). |
| Adenovirus, including all serotypes. | GENBANK Acc. Nos. AY803294; NC_004001; AC_000019; AC_000018; AC_000017; AC_000015; AC_000008; AC_000007; AC_000006; AC_000005; AY737798; AY737797; NC_003266; NC_002067; AY594256; AY594254; AY875648; AJ854486; AY163756; AY594255; |

TABLE 2-continued

| Antigen | Reference |
|---|---|
| | AY594253; NC_001460; NC_001405; AY598970; AY458656; AY487947; NC_001454; AF534906; AY45969; AY128640; L19443; AY339865; AF532578. |
| Filoviruses, including Marburg virus and Ebola virus, and strains such as Ebola-Sudan (EBO-S), Ebola-Zaire (EBO-Z), and Ebola-Reston (EBO-R). | See, e.g., Geisbert and Jahrling (1995) *Virus Res.* 39: 129-150; Hutchinson, et al. (2001) *J. Med. Virol.* 65: 561-566. Marburg virus (see, e.g., GENBANK Acc. No. NC_001608). Ebola virus (see, e.g., GENBANK Acc. Nos. NC_006432; AY769362; NC_002549; AF272001; AF086833). |
| Arenaviruses, including lymphocytic choriomeningitis (LCM) virus, Lassa virus, Junin virus, and Machupo virus. | Junin virus, segment S (GENBANK Acc. No. NC_005081); Junin virus, segment L (GENBANK Acc. No. NC_005080). |
| Rabies virus. | See, e.g., GENBANK Acc. Nos. NC_001542; AY956319; AY705373; AF499686; AB128149; AB085828; AB009663. |
| Arboviruses, including West Nile virus, Dengue viruses 1 to 4, Colorado tick fever virus, Sindbis virus, Togaviraidae, Flaviviridae, Bunyaviridae, Reoviridae, Rhabdoviridae, Orthomyxoviridae, and the like. | Dengue virus type 1 (see, e.g., GENBANK Acc. Nos. AB195673; AY762084). Dengue virus type 2 (see, e.g., GENBANK Acc. Nos. NC_001474; AY702040; AY702039; AY702037). Dengue virus type 3 (see, e.g., GENBANK Acc. Nos. AY923865; AT858043). Dengue virus type 4 (see, e.g., GENBANK Acc. Nos. AY947539; AY947539; AF326573). Sindbis virus (see, e.g., GENBANK Acc. Nos. NC_001547; AF429428; J02363; AF103728). West Nile virus (see, e.g., GENBANK Acc. Nos. NC_001563; AY603654). |
| Poxvirus including orthopoxvirus (variola virus, monkeypox virus, vaccinia virus, cowpox virus), yatapoxvirus (tanapox virus, Yaba monkey tumor virus), parapoxvirus, and molluscipoxvirus. | Viriola virus (see, e.g., GENBANK Acc. Nos. NC_001611; Y16780; X72086; X6198). |
| Yellow fever. | See, e.g., GENBANK Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) *J. Clin. Microbiol.* 35: 1122-1130; Sjolander, et al. (2002) *Epidemiol. Infect.* 128: 99-103; Zeier, et al. (2005) *Virus Genes* 30: 157-180. GENBANK Acc. No. NC_005222 and NC_005219 (Hantavirus). See also, e.g., GENBANK Acc. Nos. NC_005218; NC_005222; NC_005219. |
| Flaviviruses, including Dengue virus, Japanese encephalitis virus, West Nile virus, and yellow fever virus. | See, e.g., Mukhopadhyay, et al. (2005) *Nature Rev. Microbiol.* 3: 13-22. GENBANK Acc. Nos. NC_001474 and AY702040 (Dengue). GENBANK Acc. Nos. NC_001563 and AY603654. |
| Measles virus. | See, e.g., GENBANK Acc. Nos. AB040874 and AY486084. |
| Human parainfluenzaviruses (HPV), including HPV types 1-56. | Human parainfluenza virus 2 (see, e.g., GENBANK Acc. Nos. AB176531; NC003443). Human parainfluenza virus 3 (see, e.g., GENBANK Acc. No. NC_001796). |
| Influenza virus, including influenza virus types A, B, and C. | Influenza nucleocapsid (see, e.g., GENBANK Acc. No. AY626145). Influenza hemagglutinin (see, e.g., GENBANK Acc. Nos. AY627885; AY555153). Influenza neuraminidase (see, e.g., GENBANK Acc. Nos. AY555151; AY577316). Influenza matrix protein 2 (see, e.g., GENBANK Acc. Nos. AY626144). Influenza basic protein 1 (see, e.g., GENBANK Acc. No. AY627897). Influenza polymerase acid protein (see, e.g., GENBANK Acc. No. AY627896). Influenza nucleoprotein (see, e.g., GENBANK Acc. No. AY627895). |
| Influenza A virus subtypes, e.g., swine viruses (SIV): H1N1 influenza A and swine influenza virus. | Hemagglutinin of H1N1 (GENBANK Acc. No. S67220). Influenza A virus matrix protein (GENBANK Acc. No. AY700216). Influenza virus A H5H1 nucleoprotein (GENBANK Acc. No. AY646426). H1N1 haemagglutinin (GENBANK Acc. No. D00837). See also, GENBANK Acc. Nos. BD006058; BD006055; BD006052. See also, e.g., Wentworth, et al. (1994) *J. Virol.* 68: 2051-2058; Wells, et al. (1991) *J.A.M.A.* 265: 478-481. |
| Respiratory syncytial virus (RSV), including subgroup A and subgroup B. | Respiratory syncytial virus (RSV) (see, e.g., GENBANK Acc. Nos. AY353550; NC_001803; NC001781). |
| Rotaviruses, including human rotaviruses A to E, bovine rotavirus, rhesus monkey rotavirus, and human-RVV reassortments. | Human rotavirus C segment 8 (GENBANK Acc. No. AJ549087); Human rotavirus G9 strain outer capsid protein (see, e.g., GENBANK Acc. No. DQ056300); Human rotavirus B strain non-structural protein 4 (see, e.g., GENBANK Acc. No. AY548957); human rotavirus A strain major inner capsid protein (see, e.g., GENBANK Acc. No. AY601554). |
| Polyomavirus, including simian virus 40 (SV40), JC virus (JCV) and BK virus (BKV). | See, e.g., Engels, et al. (2004) *J. Infect. Dis.* 190: 2065-2069; Vilchez & Butel (2004) *Clin. Microbiol. Rev.* 17: 495-508; Shivapurkar, et al. (2004) *Cancer Res.* 64: 3757-3760; Carbone, et al. (2003) *Oncogene* 2: 5173-5180; Barbanti-Brodano, et al. (2004) |

TABLE 2-continued

| Antigen | Reference |
|---|---|
| | Virology 318: 1-9) (SV40 complete genome in, e.g., GENBANK Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79: 2481-2489. Segments of Eyach virus (see, e.g., GENBANK Acc. Nos. AF282475; AF282472; AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Calciviruses, including the genogroups Norwalk, Snow Mountain group (SMA), and Saaporo. | Snow Mountain virus (see, e.g., GENBANK Acc. No. AY134748). |
| Parvoviridae, including dependovirus, parvovirus (including parvovirus B19), and erythrovirus. | See, e.g., Brown (2004) Dev. Biol. (Basel) 118: 71-77; Alvarez-Lafuente, et al. (2005) Ann. Rheum. Dis. 64: 780-782; Ziyaeyan, et al. (2005) Jpn. J. Infect. Dis. 58: 95-97; Kaufman, et al. (2005) Virology 332: 189-198. |

Other organisms for which suitable antigens are known in the art include, but are not limited to, *Chlamydia trachomatis*, *Streptococcus pyogenes* (Group A Strep), *Streptococcus agalactia* (Group B Strep), *Streptococcus pneumonia*, *Staphylococcus aureus*, *Escherichia coli*, *Haemophilus influenzae*, *Neisseria meningitidis*, *Neisseria gonorrheae*, *Vibrio cholerae*, *Salmonella* species (including *typhi*, *typhimurium*), enterica (including *Helicobactor pylori Shigella flexneri* and other Group D *shigella* species), *Burkholderia mallei*, *Burkholderia pseudomallei*, *Klebsiella pneumonia*, *Clostridium* species (including *C. difficile*), *Vibrio parahaemolyticus* and *V. vulnificus*.

In certain embodiments, antigen sequence(s) may be expressed as full-length proteins, or as antigenic fragments thereof. The antigens or antigenic fragments can be expressed for secretion, e.g., by including a *L. monocytogenes* secretory sequence. Alternatively, antigenic sequence(s) can be expressed as a single polypeptide fused to a portion of the *L. monocytogenes* virulence determinant protein which permits expression and secretion of a fusion protein from the bacterium within the vaccinated host. In these embodiments, the antigenic construct may be a nucleic acid molecule including a promoter operably linked to a nucleic acid molecule encoding a fusion protein, wherein the fusion protein includes (a) virulence determinant such as ActA, phospholipase C (plcA or plcB), an internalin (InlA or InlB), p60, or listeriolysin and (b) one or more antigenic epitopes to be expressed as a fusion protein following the virulence determinant sequence. For example, the exogenous antigen can be used to a truncated form of listeriolysin. See, US 2003/0202985.

As sequences encoded by one organism are not necessarily codon optimized for optimal expression in a chosen vaccine platform bacterial strain, the present invention also provides nucleic acids that are altered by codon optimized for expression by *L. monocytogenes*.

The invention supplies a number of *Listeria* species and strains for making or engineering an attenuated bacterium of the present invention. By way of illustration, the *Listeria* of the present invention may include, but is not limited to, the strains disclosed in Table 3.

TABLE 3

| Strain | Reference |
|---|---|
| *L. monocytogenes* 10403S wild type. | Bishop & Hinrichs (1987) J. Immunol. 139: 2005-2009; Lauer, et al. (2002) J. Bact. 184: 4177-4186. |
| *L. monocytogenes* DP-L4056 (phage cured). | Lauer, et al. (2002) J. Bact. 184: 4177-4186. |
| *L. monocytogenes* DP-L4027, which is DP-L2161, phage cured, deleted in hly gene. | Lauer, et al. (2002) J. Bact. 184: 4177-4186; Jones and Portnoy (1994) Infect. Immunity 65: 5608-5613. |
| *L. monocytogenes* DP-L4042 (delta PEST) | Brockstedt, et al. (2004) Proc. Natl. Acad. Sci. USA 101: 13832-13837. |
| *L. monocytogenes* DP-L4097 (LLO-S44A). | Brockstedt, et al. (2004) Proc. Natl. Acad. Sci. USA 101: 13832-13837. |
| *L. monocytogenes* DP-L4364 (delta lplA; lipoate protein ligase). | Brockstedt, et al. (2004) Proc. Natl. Acad. Sci. USA 101: 13832-13837. |
| *L. monocytogenes* DP-L4405 (delta inlA). | Brockstedt, et al. (2004) Proc. Natl. Acad. Sci. USA 101: 13832-13837. |
| *L. monocytogenes* DP-L4406 (delta inlB). | Brockstedt, et al. (2004) Proc. Natl. Acad. Sci. USA 101: 13832-13837. |
| *L. monocytogenes* CS-L0003 (L461T-delta lplA). | Brockstedt, et al. (2004) Proc. Natl. Acad. Sci. USA 101: 13832-13837. |
| *L. monocytogenes* DP-L4384 (S44A-LLO L461T). | Brockstedt, et al. (2004) Proc. Natl. Acad. Sci. USA 101: 13832-13837. |
| *L. monocytogenes*. Mutation in lipoate protein ligase (LplA1). | O'Riordan, et al. (2003) Science 302: 462-464. |
| *L. monocytogenes* DP-L4017 (10403S hly (L461T) point mutation in hemolysin gene. | U.S. Pat. No. 7,695,725. |
| *L. monocytogenes* EGD. | GENBANK Acc. No. AL591824. |
| *L. monocytogenes* EGD-e. | GENBANK Acc. No. NC_003210. ATCC Acc. No. BAA-679. |
| *L. monocytogenes* strain EGD, complete genome, segment 3/12 | GENBANK Acc. No. AL591975 |
| *L. monocytogenes*. | ATCC Nos. 13932; 15313; 19111-19120; 43248-43251; 51772-51782. |
| *L. monocytogenes* DP-L4029 deleted in uvrAB. | U.S. Pat. No. 7,695,725. |
| *L. monocytogenes* DP-L4029 deleted in uvrAB treated with a psoralen. | U.S. Pat. No. 7,695,725. |
| *L. monocytogenes* lplA mutant or hly mutant. | US 2004/0013690 |
| *L. monocytogenes* DAL/DAT double mutant. | US 2005/0048081 |
| *L. monocytogenes* str. 4b F2365. | GENBANK Acc. No. NC_002973. |

The invention also includes the use of *L. monocytogenes* prsA2 htrA deletion mutant in the manufacture of a medicament for raising an immune response in an animal. The medicament is preferably an immunogenic composition (e.g. a vaccine), and will include, in addition to the deletion mutant of the invention, an antigen against which an immune response is to be raised.

Given that the attenuated *L. monocytogenes* prsA2 htrA deletion mutant of this invention stimulates robust dendritic cell activation, robust host immune response that can mediate robust protective immunity, this invention also provides a method for eliciting an immune response by administering to a subject in need thereof an effective amount of a vaccine containing the attenuated *L. monocytogenes* mutant optionally containing one or more nucleic acid molecules encoding exogenous antigens. The immune response can include, without limitation, a specific immune response, a non-specific immune response, both specific and non-specific responses, an innate response, a primary immune response, an adaptive immunity, a secondary immune response, a memory immune response, immune cell activation, immune cell proliferation, immune cell differentiation, a protective immune response and/or cytokine expression. In certain embodiments, a protective immune response is elicited.

In certain embodiments, after the subject has been administered an effective dose of a first vaccine to prime the immune response, a second vaccine is administered. This is referred to in the art as a "prime-boost" regimen. In such a regimen, the compositions and methods of the present invention may be used as the "prime" delivery, as the "boost" delivery, or as both a "prime" and a "boost." Any number of "boost" immunizations can be delivered in order to maintain the magnitude or effectiveness of a vaccine-induced immune response.

As an example, a first vaccine composed of killed but metabolically active *Listeria* that encodes and expresses one or more antigen polypeptide(s) may be delivered as the "prime," and a second vaccine composed of attenuated (live or killed but metabolically active) *Listeria* that encodes the antigen polypeptide(s) may be delivered as the "boost." It should be understood, however, that each of the prime and boost need not utilize the methods and compositions of the present invention. Rather, the present invention contemplates the use of other vaccine modalities together with the *Listeria* vaccine methods and compositions of the present invention. The following are examples of suitable mixed prime-boost regimens: a DNA (e.g., plasmid) vaccine prime/bacterial vaccine boost; a viral vaccine prime/bacterial vaccine boost; a protein vaccine prime/bacterial vaccine boost; a DNA prime/bacterial vaccine boost plus protein vaccine boost; a bacterial vaccine prime/DNA vaccine boost; a bacterial vaccine prime/viral vaccine boost; a bacterial vaccine prime/protein vaccine boost; a bacterial vaccine prime/bacterial vaccine boost plus protein vaccine boost; etc.

The prime vaccine and boost vaccine may be administered by the same route or by different routes. The term "different routes" encompasses, but is not limited to, different sites on the body, for example, a site that is oral, non-oral, enteral, parenteral, rectal, intranode (lymph node), intravenous, arterial, subcutaneous, intradermal, intramuscular, intratumor, peritumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine or vaccines in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on.

In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

In certain embodiments, administration of the boost vaccination can be initiated at about 5 days after the prime vaccination is initiated; about 10 days after the prime vaccination is initiated; about 15 days; about 20 days; about 25 days; about 30 days; about 35 days; about 40 days; about 45 days; about 50 days; about 55 days; about 60 days; about 65 days; about 70 days; about 75 days; about 80 days, about 6 months, and about 1 year after administration of the prime vaccination is initiated. Preferably one or both of the prime and boost vaccination comprises delivery of a composition of the present invention.

Administration of the vaccine of the present invention by a non-oral route can avoid tolerance. Methods are known in the art for administration intravenously, subcutaneously, intradermally, intramuscularly, intraperitoneally, orally, mucosally, by way of the urinary tract, by way of a genital tract, by way of the gastrointestinal tract, or by inhalation.

An effective amount for a particular subject may vary depending on factors such as the condition being treated, the overall health of the patient, the route and dose of administration and the severity of side effects. Guidance for methods of treatment and diagnosis is available (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

The vaccines of the present invention can be administered in a dose, or dosages, where each dose includes at least 100 bacterial cells/kg body weight or more; in certain embodiments 1000 bacterial cells/kg body weight or more; normally at least 10,000 cells; more normally at least 100,000 cells; most normally at least 1 million cells; often at least 10 million cells; more often at least 100 million cells; typically at least 1 billion cells; usually at least 10 billion cells; conventionally at least 100 billion cells; and sometimes at least 1 trillion cells/kg body weight. The present invention provides the above doses where the units of bacterial administration is colony forming units (CFU) or where the units are number of bacterial cells.

The vaccines of the present invention can be administered in a dose, or dosages, where each dose includes between $10^7$ and $10^8$ bacteria per 70 kg body weight (or per 1.7 square meters surface area; or per 1.5 kg liver weight); $2 \times 10^7$ and $2 \times 10^8$ bacteria per 70 kg body weight (or per 1.7 square meters surface area; or per 1.5 kg liver weight); $5 \times 10^7$ and $5 \times 10^8$ bacteria per 70 kg body weight (or per 1.7 square meters surface area; or per 1.5 kg liver weight); $10^8$ and $10^9$ bacteria per 70 kg body weight (or per 1.7 square meters surface area; or per 1.5 kg liver weight); between $2.0 \times 10^8$ and $2.0 \times 10^9$ bacteria per 70 kg (or per 1.7 square meters surface area, or per 1.5 kg liver weight); between $5.0 \times 10^8$ to $5.0 \times 10^9$ bacteria per 70 kg (or per 1.7 square meters surface area, or per 1.5 kg liver weight); between $10^9$ and $10^{10}$ bacteria per 70 kg (or per 1.7 square meters surface area, or per 1.5 kg liver weight); between $2 \times 10^9$ and $2 \times 10^{10}$ bacteria per 70 kg (or per 1.7 square meters surface area, or per 1.5 kg liver weight); between $5\times10^9$ and $5\times10^{10}$ ° bacteria per 70 kg (or per 1.7 square meters surface area, or per 1.5 kg liver weight); between $10^{11}$ and $10^{12}$ bacteria per 70 kg (or per 1.7 square meters surface area, or per 1.5 kg liver weight); between $2\times10^{11}$ and $2\times10^{12}$ bacteria per 70 kg (or per 1.7 square meters surface area, or per 1.5 kg liver weight); between $5\times10^{11}$ and $5\times10^{12}$ bacteria per 70 kg (or per 1.7 square meters surface area, or per 1.5 kg liver weight); between $10^{12}$ and $10^{13}$ bacteria per 70 kg (or per 1.7 square meters surface area); between $2\times10^{12}$ and $2\times10^{13}$ bacteria per 70 kg (or per 1.7 square meters surface area, or per 1.5 kg liver weight); between $5\times10^{12}$ and $5\times10^{13}$ bacteria per 70 kg (or per 1.7 square meters surface area, or per 1.5 kg liver weight); between $10^{13}$ and $10^{14}$ bacteria per 70 kg (or per 1.7 square meters surface area, or per 1.5 kg liver weight); between $2\times10^{13}$ and $2\times10^{14}$ bacteria per 70 kg (or per 1.7 square meters surface area, or per 1.5 kg liver weight); $5\times10^{13}$ and $5\times10^{14}$ bacteria per 70 kg (or per 1.7 square meters surface area, or per 1.5 kg liver weight); between $10^{14}$ and $10^{15}$ bacteria per 70 kg (or per 1.7 square meters surface area, or per 1.5 kg liver weight); between $2\times10^{14}$ and $2\times10^{15}$ bacteria per 70 kg (or per 1.7 square meters surface area, or per 1.5 kg liver weight); and so on, wet weight.

Also provided is one or more of the above doses, where the dose is administered by way of one injection every day, one injection every two days, one injection every three days, one injection every four days, one injection every five days, one injection every six days, or one injection every seven days, where the injection schedule is maintained for, e.g., one day only, two days, three days, four days, five days, six days, seven days, two weeks, three weeks, four weeks, five weeks, or longer. The invention also embraces combinations of the above doses and schedules, e.g., a relatively large initial bacterial dose, followed by relatively small subsequent doses, or a relatively small initial dose followed by a large dose.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

The present invention encompasses a method of administering an attenuated L. monocytogenes prsA2 htrA deletion mutant that is oral. Also provided is a method of administering an attenuated L. monocytogenes prsA2 htrA deletion mutant that is intravenous. Moreover, what is provided is a method of administering an attenuated L. monocytogenes prsA2 htrA deletion mutant that is oral, intramuscular, intravenous, intradermal, intraperitoneally, mucosally and/or subcutaneous, as well as by way of the urinary tract, genital tract, gastrointestinal tract or inhalation.

For use in the vaccines and compositions of this invention, the attenuated L. monocytogenes prsA2 htrA deletion mutant can be grown in a medium that is meat based, or that contains polypeptides derived from a meat or animal product. Alternatively, the bacterium can be grown in a medium that does not contain meat or animal products. Such medium can be contain vegetable polypeptides or yeast polypeptides. The bacteria grown in the medium can be harvested or isolated and resuspended in the carrier, e.g., water, saline, phosphate buffered solutions or bicarbonate buffered solutions.

The attenuated L. monocytogenes prsA2 htrA deletion mutant optionally including one or more exogenous antigens can be administered alone or in combination with an additional agent, e.g., a costimulatory agent or therapeutic agent. Methods for co-administration with an additional therapeutic agent are well known in the art (Hardman, et al. (eds.) (2001) *Goodman and Gilman's The Pharmacological Basis of Therapeutics*, 10th ed., McGraw-Hill, New York, N.Y.; Poole and Peterson (eds.) (2001) *Pharmacotherapeutics for Advanced Practice: A Practical Approach*, Lippincott, Williams & Wilkins, Phila., Pa.; Chabner & Longo (eds.) (2001) *Cancer Chemotherapy and Biotherapy*, Lippincott, Williams & Wilkins, Phila., Pa.).

Additional agents which are beneficial to raising a cytolytic T cell response may be used as well. Such agents are termed herein costimulatory agents. These include, without limitation, B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Costimulatory agents for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The costimulatory agent can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The costimulatory agent can be a bacterial cell that is transformed to express the polypeptide or to deliver a polynucleotide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, and other like immune modulators such as cyclic dinucleotide STING agonists including c-di-GMP, c-di-AMP, c-di-IMP, and c-AMP-GMP, used separately or in combination with the described compositions are also potential adjuvants. Other representative examples of adjuvants include the synthetic adjuvant QS-21 comprising a homogeneous saponin purified from the bark of *Quillaja saponaria* and *Corynebacterium parvum* (McCune et al. (1979) *Cancer* 43:1619). It will be understood that the adjuvant is subject to optimization. In other words, the skilled artisan can engage in routine experimentation to determine the best adjuvant to use.

Therapeutic agents include, but are not limited to, antivirals, antibacterials, antiparasitics, and chemotherapeutic agents such as cytoxic agents, alkylating agents, biologics (antibodies, immunotoxins, or growth factor linked toxins), anti-angiogenesis agents and radiosensitizers.

In addition to a vaccine, the invention also supplies a pharmaceutical composition containing an attenuated *L. monocytogenes* prsA2 htrA deletion mutant bacterial culture suspended in a pharmaceutically acceptable carrier. In some embodiments, the attenuated *L. monocytogenes* prsA2 htrA deletion mutant further includes in its genome one or more nucleic acid molecules encoding exogenous antigens.

The attenuated *L. monocytogenes* prsA2 htrA deletion mutant, pharmaceutical composition or vaccine of the invention can be employed in various methods for preventing and/or treating a disease or condition. In particular embodiments, the invention provides a method for preventing or treating cancer or an infection by administering to a subject in need thereof an effective amount of a vaccine or pharmaceutical composition containing an attenuated *L. monocytogenes* prsA2 htrA deletion mutant optionally including one or more nucleic acid molecules encoding exogenous antigens. Cancers that can be prevented or treated with the instant attenuated mutant, pharmaceutical composition or vaccine include, but are not limited to, primary or secondary cancers of the brain, skin, pancreas, liver, ovary, breast, prostate, lung, colon, cervix, bone, bladder, stomach, testis, thyroid, kidney, throat, mouth, uterus, rectum or esophagus. Examples of infections include bacterial, fungal, viral and parasitic infections, e.g., as described above.

An effective amount, as used in the context of the instant invention, is an amount which produces a detectable immune response (e.g., a Th-1 response, natural granulocyte, neutrophil, macrophage, GR1+ macrophage, B cell, or T cell immune response) and reduces or prevents the signs or symptoms of cancer or infection. In accordance with some embodiments, the attenuated *L. monocytogenes* prsA2 htrA deletion mutant expresses an exogenous antigen thereby generating protective immunity against the cancer or infectious agent from which the antigen was derived or associated. However, in other embodiments, the attenuated *L. monocytogenes* prsA2 htrA deletion mutant of the invention alone is sufficient to generate an immune response thereby treating or having an effect on the severity of the cancer or infection.

While the instant compositions and methods find application in the prevention and treatment of cancer or infection in mammals, in particular humans, the invention should be construed to include administration to a variety of animals, including, but not limited to, cats, dogs, horses, cows, cattle, sheep, goats, birds such as chickens, ducks, and geese. Subjects benefiting from prophylactic or therapeutic treatment with the instant attenuated mutant include subjects with a positive diagnosis of early or late stage cancer, subjects at risk of developing cancer (e.g., because of family history or exposure to a carcinogen), subjects who have had successful treatment of a primary tumor and are at risk of developing or have developed a secondary or metastatic tumor, subjects with a positive diagnosis of an infection, or subjects at risk of having being exposed to an infectious agent.

The following non-limiting examples are provided to further illustrate the present invention.

EXAMPLE 1

Preparation and Analysis of *L. monocytogenes* prsA2 htrA Deletion Mutant

The NF-L1633 strain of *L. monocytogenes* lacks two secreted chaperone proteins that assist the folding and activity of secreted bacterial proteins. HtrA, encoded by htrA, is a secreted chaperone that also possesses protease activity. PrsA2, encoded by prsA2, is a chaperone that is required for the folding and activity of a number of *L. monocytogenes* secreted virulence factors.

The preparation and isolation of *L. monocytogenes* prsA2 htrA deletion mutant (ΔhtrA ΔprsA2) is described in the art (Alonzo, III & Freitag (2010) *Infect. Immun.* 70(11):4944-4257). U153 bacteriophage-mediated transduction was performed as previously described (Alonzo, III et al. (2009) *Infect. Immun.* 77:2612-2623; Wong & Freitag (2004) *J. Bacteriol.* 186:6265-6276). Briefly, phage lysates were prepared from the *L. monocytogenes* ΔprsA2:: erm mutant (NF-L1651; Alonzo, III et al. (2009) *Infect. Immun.* 77:2612-2623). Lysates were mixed at a 1:1 ratio with ΔhtrA (NF-L1605) mutant strain ($10^8$ phage to $10^8$ CFU) and incubated at room temperature for 40 minutes in the presence of $CaCl_2$ and $MgCl_2$ (final concentration, 10 mM). Mixtures of bacteria and bacteriophage lysates were then spread onto BHI plates containing 1 μg/ml erythromycin to select for transductants. For each transductant, the replacement of the wild-type prsA2 allele with the prsA2::erm mutation was confirmed by PCR amplification of the appropriate chromosomal region. Confirmed mutant strains were designated ΔhtrA ΔprsA2 (NF-L1633) double mutants.

Mouse Intravenous Infections. Bacterial cells were prepared as previously described (Alonzo, III et al. (2009) *Infect. Immun.* 77:2612-23). Female Swiss Webster mice (6 to 8 weeks old) were inoculated via the tail vein with 200 μl phosphate-buffered saline (PBS) containing $2 \times 10^4$ CFU of each bacterial strain tested. After 72 hours, mice were sacrificed and both the liver and spleen were isolated. Each organ was homogenized in 5 ml of $H_2O$ using a Tissue Master 125 homogenizer (Omni; Marietta, Ga.), and dilutions were spread onto BHI agar plates to quantify the bacterial burden in each organ.

Figure 1B:
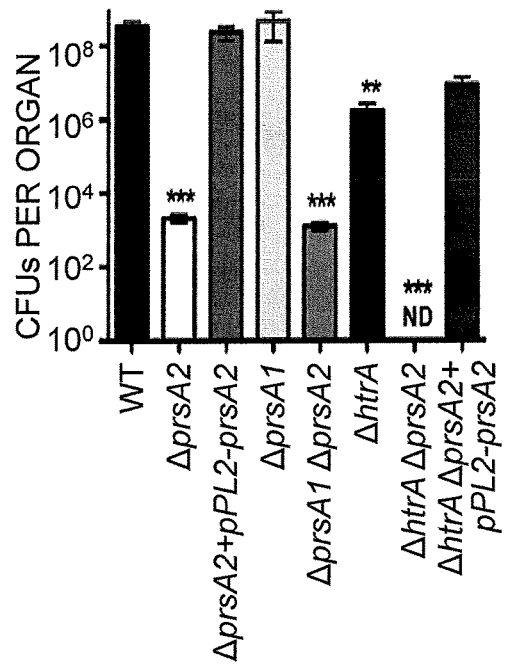

The results of this analysis indicated that the NF-L1633 mutant strain was highly attenuated for virulence (FIGS. 1A and 1B), such that mice infected with the mutant were able to completely clear the mutant by three days post-infection. The htrA prsA2 double deletion strain was capable of invading host cells and reaching the cytosol, however the bacteria rapidly lost viability within the cytosol.

Figure 2A:
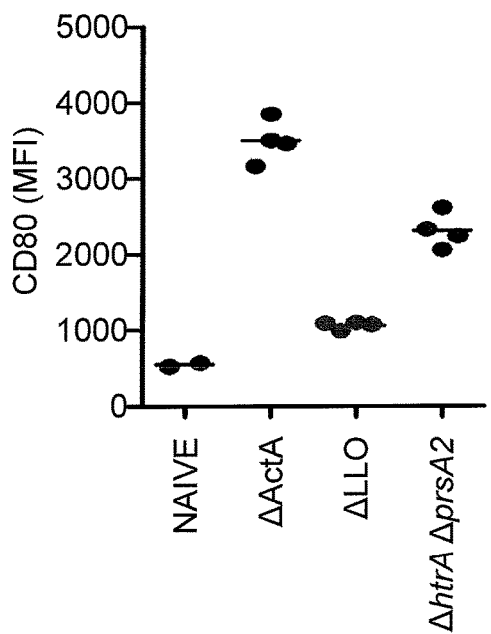
FIGS. 2A and 2B show that *L. monocytogenes* prsA2 htrA deletion mutant induces dendritic cell maturation. C57BL/6 mice were vaccinated once with an injection through the tail vein with $10^5$ CFU of the *L. monocytogenes* actA mutant or $10^8$ CFU of the *L. monocytogenes* hly or prsA2/htrA mutant. Then, 48 hours later, expression of the co-stimulation molecules CD80 (FIG. 2A) and CD70 (FIG. 2B) were assessed on $CD11c^+$ $MHCII^+$ dendritic cells from the spleens of infected mice. Each dot represents an individual mouse with the lines indicating the group mean.
Figure 2B:
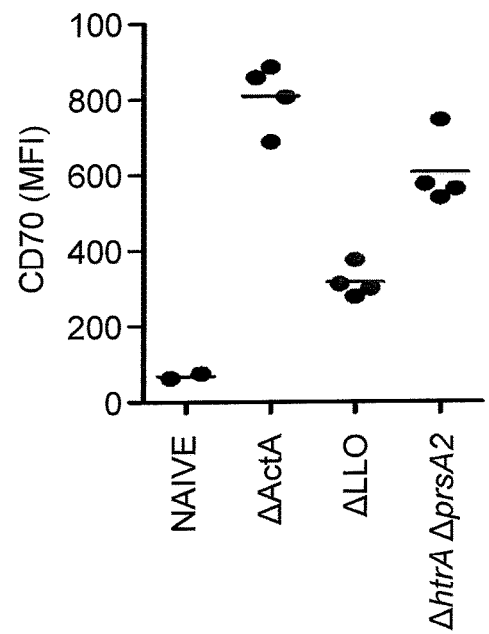
Figure 3A:
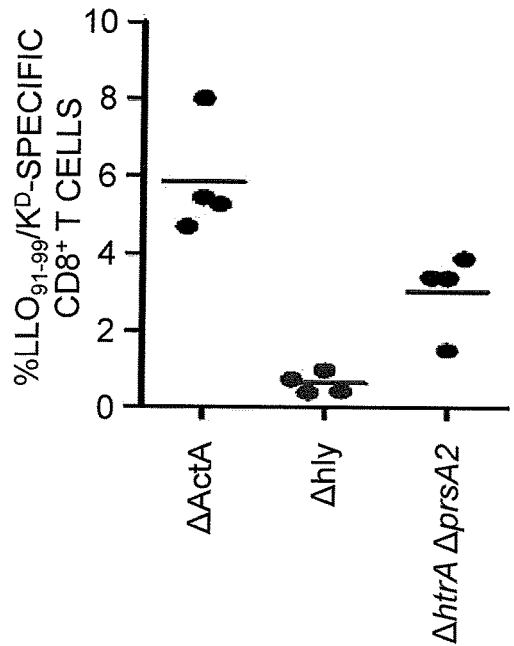
FIGS. 3A and 3B show that *L. monocytogenes* prsA2 htrA deletion mutant induces robust CD8 T cell response. BALB/c mice were injected through the tail vein with $10^5$ CFU of the *L. monocytogenes* actA mutant or $10^8$ CFU of the *L. monocytogenes* hly or prsA2/htrA mutant. Then 7 days (FIG. 3A) or 42 days (FIG. 3B) post-infection, the frequency of *L. monocytogenes*-specific CD8 T cells in the spleen was determined. Each dot represents an individual mouse with the lines indicating the group mean.
Figure 3B:
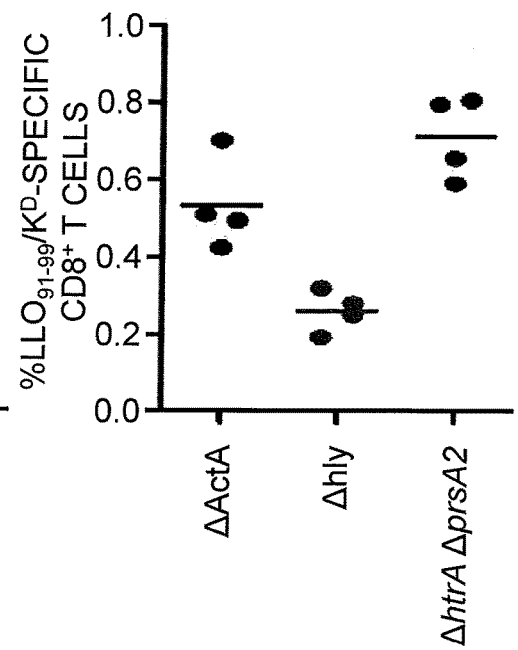
Figure 4:
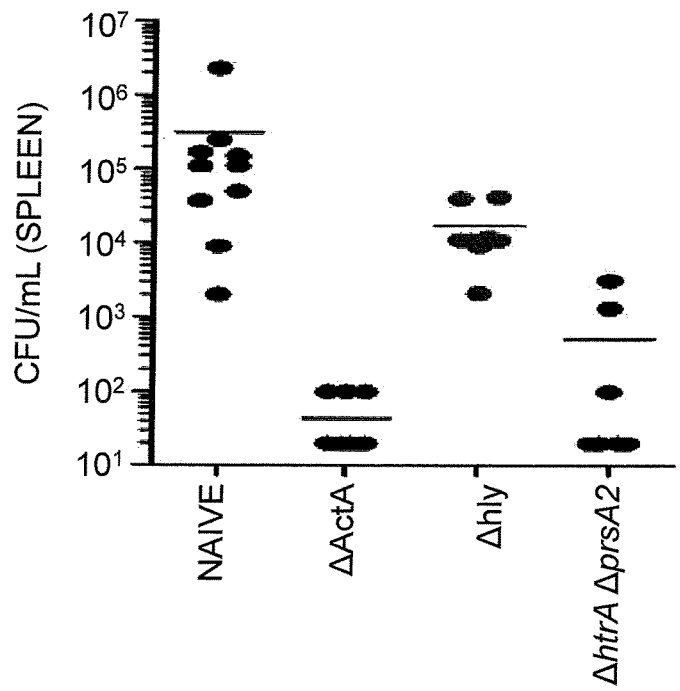
FIG. 4 shows that *L. monocytogenes* prsA2 htrA deletion mutant induces strong protective immunity. C57BL/6 mice were vaccinated once with an injection through the tail vein with $10^5$ CFU of the *L. monocytogenes* actA mutant or $10^8$ CFU of the *L. monocytogenes* hly or prsA2/htrA mutant. Then, 42 days later, each group of age-matched mice were challenged with $5\times10^5$ CFU of the virulent 10403S *L. monocytogenes* strain. The spleens of infected mice were recovered 72 hours after challenge and the bacterial burden in each organ was determined. Each dot represents an individual mouse with the lines indicating the group mean.

This analysis indicated that the *L. monocytogenes* prsA2 htrA deletion mutant would be an ideal vaccine candidate because it is highly attenuated; can escape the phagosome and express it entire repertoire of proteins; and produce a large number of mis-folded proteins, which can be an important source of antigens for T cells. Indeed, it appears the *L. monocytogenes* prsA2 htrA deletion mutant, despite its high level of attenuation, stimulates robust dendritic cell activation (FIGS. 2A and 2B), robust host immune response (FIGS. 3A and 3B) that can mediate robust protective immunity (FIG. 4). This high level of immunity was generated with a single injection of the *L. monocytogenes* prsA2 htrA deletion mutant. Given that *L. monocytogenes* does not induce robust neutralizing antibody responses, the prsA2 htrA deletion mutant can enhance immunity and increase immune conversion by homologous boosting.

What is claimed is:

1. A vaccine comprising an attenuated *Listeria monocytogenes* prsA2 htrA deletion mutant in an amount of $10^6$ to $10^{12}$ colony forming units, which produces a detectable immune response, and a carrier, wherein the mutant further comprises in its genome one or more nucleic acid molecules encoding exogenous antigens.

2. The vaccine of claim 1, wherein the antigens comprise bacterial, viral, fungal, parasitic or tumor antigens.

3. A method for eliciting an immune response comprising administering to a subject in need thereof an effective amount of the vaccine of claim 1 thereby generating an immune response to the vaccine.

4. A composition comprising an attenuated *Listeria monocytogenes* prsA2 htrA deletion mutant in an amount of $10^6$ to $10^{12}$ colony forming units, which produces a detectable immune response, and a pharmaceutically acceptable carrier, wherein the mutant further comprises in its genome one or more nucleic acid molecules encoding exogenous antigens.

* * * * *